(12) United States Patent
Bennett et al.

(10) Patent No.: US 7,629,120 B2
(45) Date of Patent: Dec. 8, 2009

(54) METHOD FOR ASSEMBLING PCR FRAGMENTS OF DNA

(75) Inventors: George Nelson Bennett, Houston, TX (US); Mary Lou Harrison, Houston, TX (US)

(73) Assignee: Rice University, Houston, TX (US)

( * ) Notice: Subject to any disclaimer, the term of this patent is extended or adjusted under 35 U.S.C. 154(b) by 1002 days.

(21) Appl. No.: 10/699,511

(22) Filed: Oct. 31, 2003

(65) Prior Publication Data

US 2005/0048514 A1    Mar. 3, 2005

Related U.S. Application Data

(60) Provisional application No. 60/422,807, filed on Oct. 31, 2002.

(51) Int. Cl.
*C12Q 1/68* (2006.01)
(52) U.S. Cl. .................... 435/6; 435/91.1; 435/91.2; 536/23.1; 536/24.33
(58) Field of Classification Search .................. None
See application file for complete search history.

(56) References Cited

U.S. PATENT DOCUMENTS 5,851,808 A * 12/1998 Elledge et al. ............. 435/91.4
2002/0007051 A1   1/2002 Cheo et al.

OTHER PUBLICATIONS

Watson and Bennet. Biotechniques vol. 23:858-864. 1997.*
Stahl et al. Biotechniques vol. 14:424-434. 1993.*
Liu et al. Current Biology vol. 8:1300-1310, S1. 1998.*
Gal J, Schnell R, Kalman M., Polymerase dependence of autosticky polymerase chain reaction, Anal Biochem. Jun. 15, 2000;282(1):156-8.
Gal J, Schnell R, Szekeres S. Kalman M., Directional cloning of native PCR products with preformed sticky ends (autosticky PCR), Mol Gen Genet. Jan. 1999; 260(6):569-73.5.
Greagg MA, Fogg MJ, Panayotou G, Evans SJ, Connolly BA, Pearl LH., A read-ahead function in archaeal DNA polymerases detects promutagenic template-strand uracil, Proc. Natl Acad Sci U S A. Aug. 3, 1999;96(16):9045-50.
Watson DE, Bennett GN. Cloning and assembly of PCR products using modified primers and DNA repair enzymes, Biotechniques. Nov. 1993;23(5):858-62, 864.
Booth PM, Buchman GW, Rashtchian A., Assembly and cloning of coding sequences for neurotrophic factors directly from genomic DNA using polymerase chain reaction and uracil DNA glycosylase, Gene. Sep 2, 1994;146(2):303-8.
Rashtchian A, Buchman GW, Schuster DM, Berninger MS.,Uracil DNA glycosylase-mediated cloning of polymerase chain reaction-amplified DNA: application to genomic and cDNA cloning, Anal Biochem. Oct. 1992;206(1):91-7.
Nisson PE, Rashtchian A, Watkins PC., Rapid and efficient cloning of Alu-PCR products using uracil DNA glycosylase, PCR Methods Appl. Nov. 1991;1(2):120-3.
Stahl S, Hansson M, Ahlborg N, Nguyen TN, Liljeqvist S, Lundeberg J, Uhlen M., Solid-phase gene assembly of constructs derived from the Plasmodium falciparum malaria blood-stage antigen Ag332, Biotechniques Mar. 1993;14(3):424-34.
Abremski K, Hoess R, Sternberg N., Studies on the properties of P1 site-specific recombination: evidence for topologically unlinked products following recombination, Cell. Apr. 1983;32(4):1301-11.

* cited by examiner

*Primary Examiner*—Jeffrey Fredman
*Assistant Examiner*—Heather G Calamita
(74) *Attorney, Agent, or Firm*—Baker & McKenzie LLP

(57) ABSTRACT

A process for assembling a series of DNA fragments generated by PCR into an ordered circular arrangement for replication and genetic work in cells. The PCR fragments are made with a modified nucleotide in the primers that can be removed with a DNA excision repair enzyme to generate a 3' overhang. The 3' overhangs are designed to allow directional annealing and thus sequential PCR fragments can be assembled by annealing the overhangs and subsequent ligation. Sequential addition of PCR fragments is facilitated by growing the chain on a solid support, and the assembled chain can be removed with a site specific recombinase if the first and last primers contain the recombinase site. The circularized assembled fragment can be directly used for cell transformation if the appropriate sequences are included, such as an origin of replication and a selectable marker.

7 Claims, 5 Drawing Sheets

METHOD FOR ASSEMBLING PCR FRAGMENTS OF DNA

PRIOR RELATED APPLICATIONS

This patent application claims priority to U.S. Provisional Application Ser. No. 60/422,807, filed on Oct. 31, 2002, the disclosure of which is incorporated by reference in its entirety herein.

FEDERALLY SPONSORED RESEARCH STATEMENT

This invention was made with government support under Grant Number BES-0000303 awarded by the National Science Foundation. The government has certain rights in the invention.

REFERENCE TO MICROFICHE APPENDIX

Not applicable.

FIELD OF THE INVENTION

A process for assembling a series of DNA fragments generated by PCR into an ordered circular arrangement for replication and genetic work in cells. The method uses the 3' overhangs created by excision repair enzymes to direct the sequential ligation of PCR fragments on a solid scaffold. The resulting assembled DNA is removed with a site specific recombinase.

BACKGROUND OF THE INVENTION

Current methods of manipulating DNA fragments are each limited by size. Plasmid sized fragments of up to 10 kb can be easily assembled, but specifically ordered fragments much larger are difficult to assemble by current techniques and require careful handling to avoid breakage. Other types of cloning vehicles allow larger fragments to be cloned and manipulated, but even these have their limits (lambda ~15-20 kb; cosmids ~35-40 kb, BAC ~100 kb and YACs ~1000 kb). Therefore, there is a need in the art for the assembly and manipulation of very large DNA fragments.

PCR fragments can be assembled into larger arrangements for useful purposes. This is usually done with the creation of restriction sites in the primer sequences. When the amplified DNA is cut with a particular restriction enzyme, a short overhang is generated that can be used to assemble two PCR fragments with complementary overhang sequences. However, PCR fragments often have like ends, so that orientation of the resulting fragment is not defined. Further, many restriction enzymes also cleave within a large PCR fragment and cannot be used in this way. When different restriction enzyme sites are used in each of the two amplification primers, the likelihood that one of restriction enzymes will cut within the PCR fragment is doubled. A method that did not depend on restriction enzymes would be of general application and advantageous.

The invention provides a means of assembling PCR fragments that does not rely on restriction enzymes.

SUMMARY OF THE INVENTION

Generally speaking, the invention uses a modified nucleotide at a specific position in the primer which is removed with DNA excision repair enzyme and AP endonuclease or AP lyase. The AP endonuclease or lyase activity may be part of the excision repair enzyme. In one embodiment the modified nucleotide is deoxyuridine and the commercially available enzymes uracil-DNA-glycosylase (4) and $T_4$ endonuclease V are used to remove the base and cleave the primer to generate a ligatable 5' phosphorylated end.

A wide variety of excision repair/AP endonuclease (or lyase) combinations are known in the art, and some of the excision repair enzymes also exhibit lyase activity, cleaving the DNA backbone on the 3' side of the AP site. Suitable excision repair enzymes include Methyl Purine DNA Glycosylase (recognizes methylated bases), 8-Oxo-Guanine Glycosylase 1 (recognizes 8-oxoG:C pairs and has lyase activity), Endonuclease Three Homolog 1 (recognizes T-glycol, C-glycol, and formamidopyrimidine and has lyase activity), inosine, hypoxanthine-DNA glycosylase; 5-Methylcytosine, 5-Methylcytosine DNA glycosylase; Formamidopyrimidine-DNA-glycosylase (excision of oxidized residue from DNA: hydrolysis of the N-glycosidic bond (DNA glycosylase), beta-elimination (AP-lyase reaction)).

Sequential ligation is facilitated if the first fragment attached to modified streptavidin-coated magnetic beads, or otherwise immobilized. Suitable immobilization methods include the use of 1) amine-oligos covalently linked to an activated carboxylate group or succinimidyl ester, 2) SH-oligos covalently linked via an alkylating reagent such as an iodoacetamide or maleimide, 3) acrydite-oligos covalently linked through a thioether, 4) antibody-antigen based capture, 5) nucleic acid triplex affinity interaction, 6) immobilized metal affinity chromatography of his-tagged DNA, 7) streptavidin-SBP-Tag, and 8) phenylboronic acid-salicylhydroxamic acid (SHA) based systems, to name a few. Several such fragments can be assembled on the solid substrate to give an in-phase, functional gene. Any substrate format may be employed.

Inclusion of a site specific recombinase site in the first and last PCR fragments of the assembled DNA allows the joined fragments to be removed from the solid assembly system and circularized for transformation. One site specific recombinase system is the cre-lox system. Inclusion of lox sites in the first (5'-most) and last (3'-most) primers, or otherwise within the amplified fragments, allows the enzyme cre to remove and circularize all DNA between the lox sites.

The cre-lox system is the most commonly used site specific recombination system, but the art teaches a very large variety of site specific recombinases that are too numerous to name. Other specific recombinases, including the FlpR, xerD, shufflon, SSV1 integrase, the Tn3 family, the IS6 family, and the lambda integrase-excisionase or terminase/cos reactions, may also be usefully adapted for the invention.

The useful features of this invention are that several fragments can be joined in a defined order allowing the PCR generated DNA fragments to be assembled into an ordered arrangement and formed into a replicating plasmid without use of restriction enzymes. The final product is in a form for transformation into cells and the use of immobilized DNA facilitates the steps and allows for scaling with automated devices.

DESCRIPTION OF EMBODIMENTS OF THE INVENTION

Figure 1:
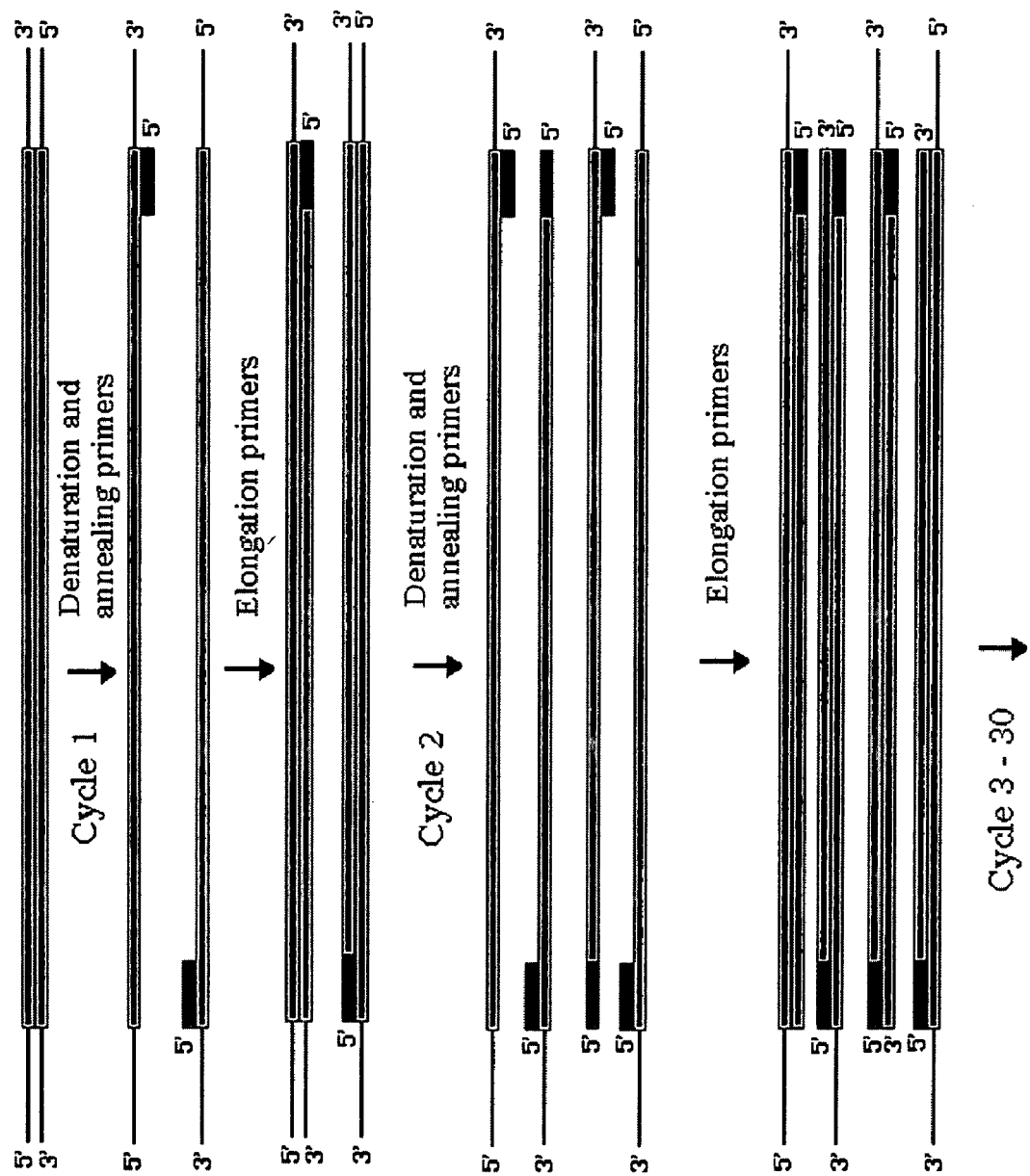
FIG. 1. Use of Modified Primers in PCR.
Figure 2:
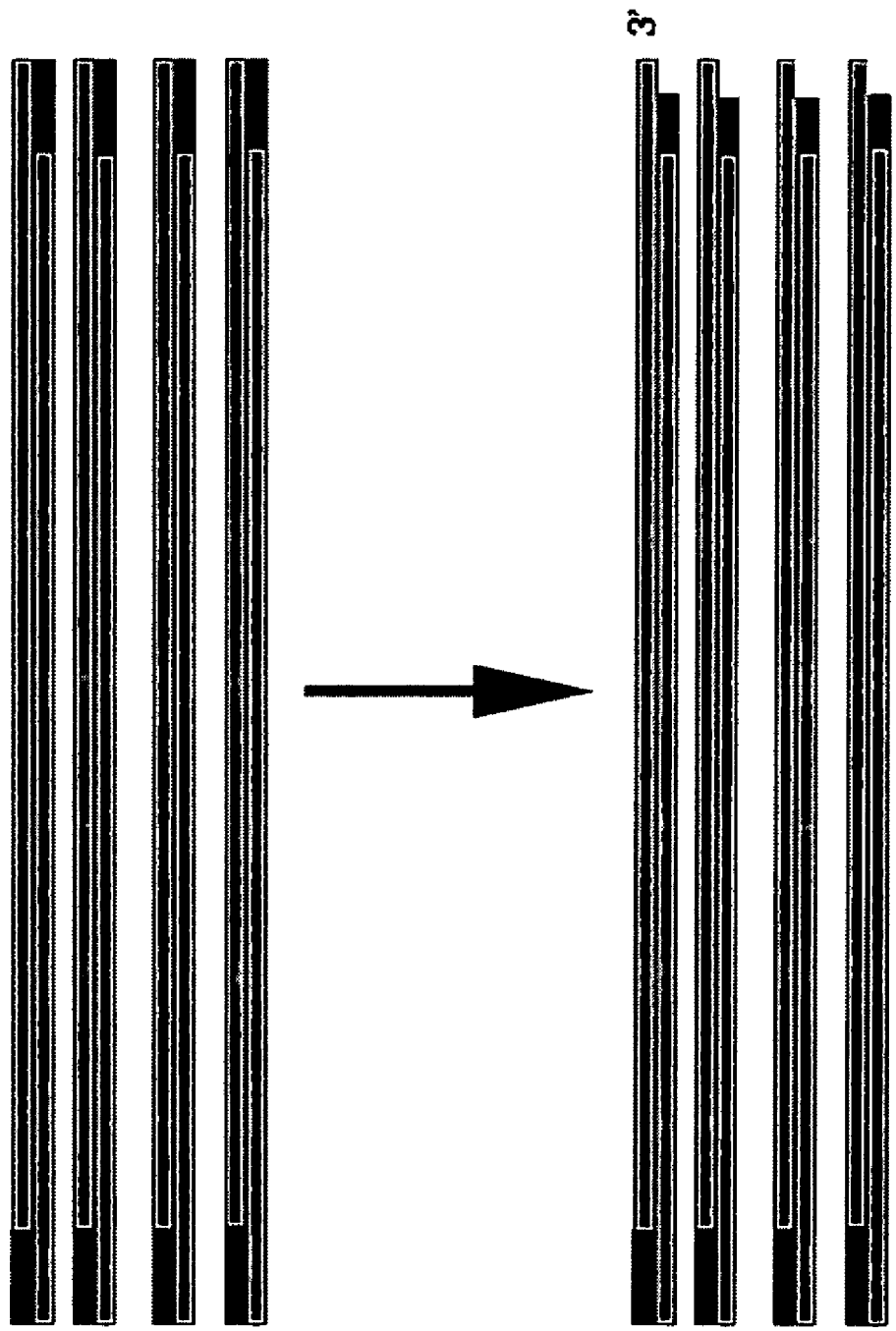
FIG. 2. After PCR the End of the Primer Can be Removed.
Figure 3:
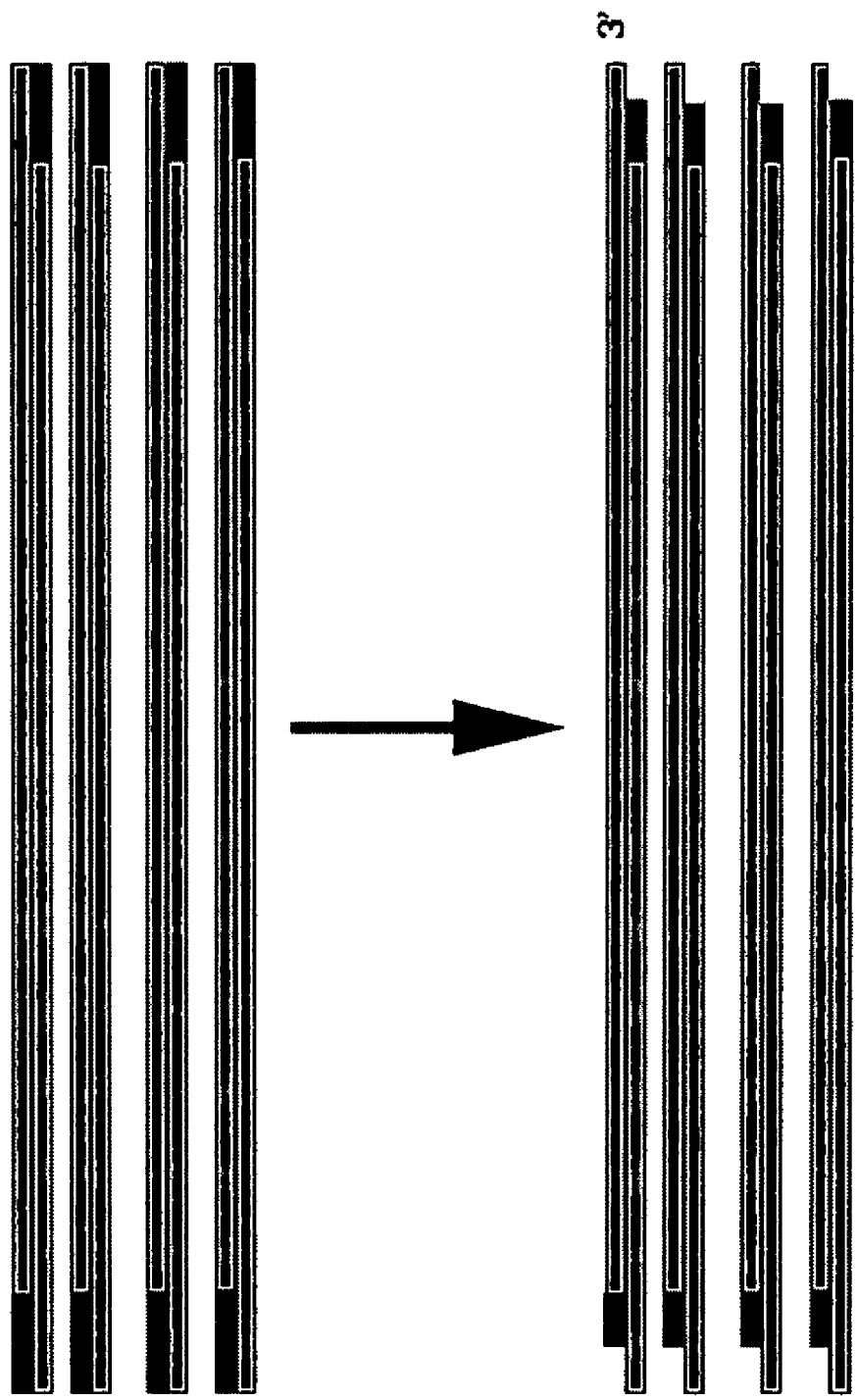
FIG. 3. The Protruding Ends can be Made at one of Both Ends of the PCR Fragment.
Figure 4:
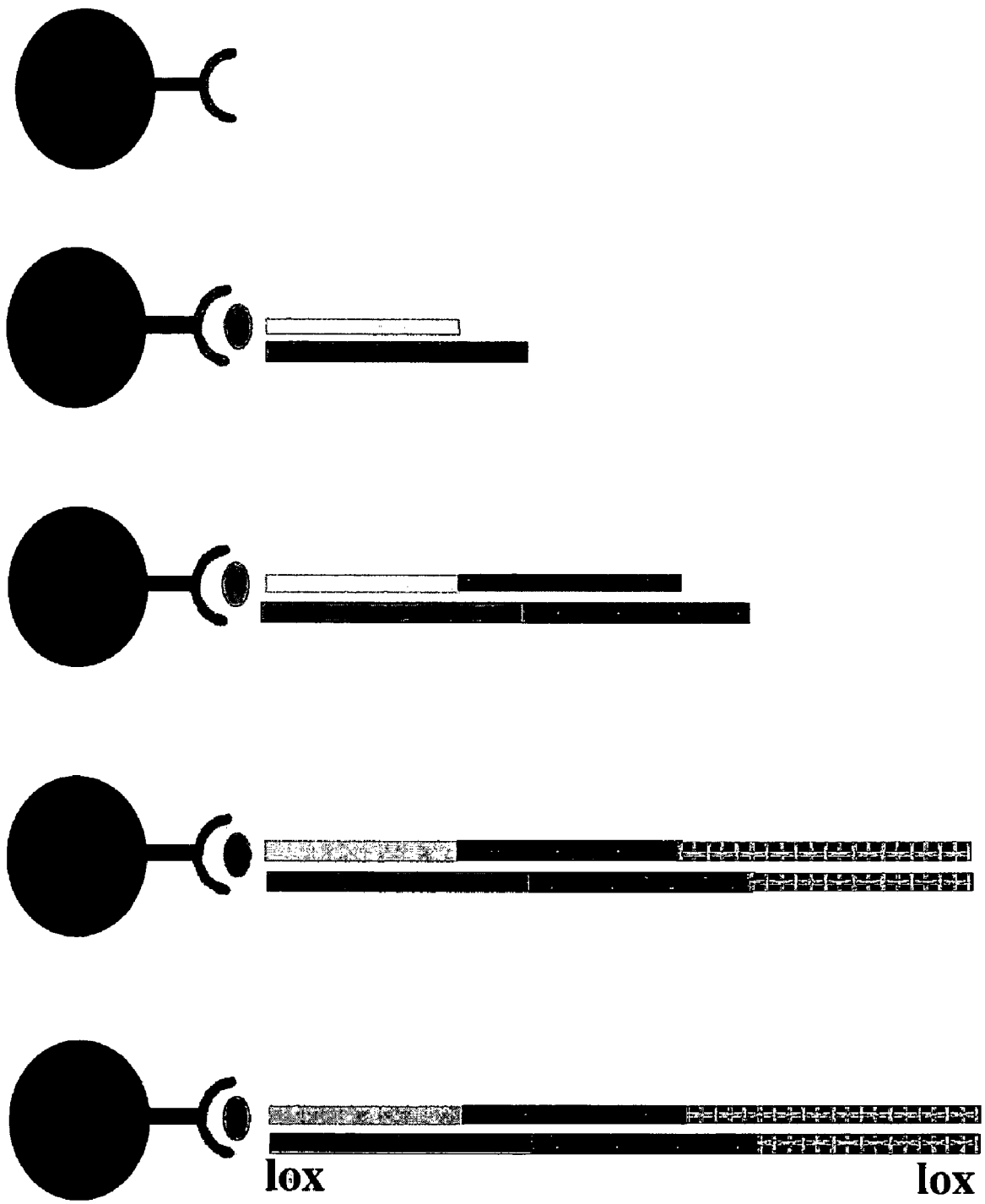
FIG. 4A Biotin can be Attached to the End of the DNA Fragment, Then Ligations can be Done Sequentially with the DNA Attached to the Bead. Lox sites are shown in the first and last primers. Treatment with CRE allows removal and circularization of the final assembled product. Also, by including replication and selection functions on the DNA between the lox sites, the DNA will form a functional vector capable of transforming cells.
Figure 5:
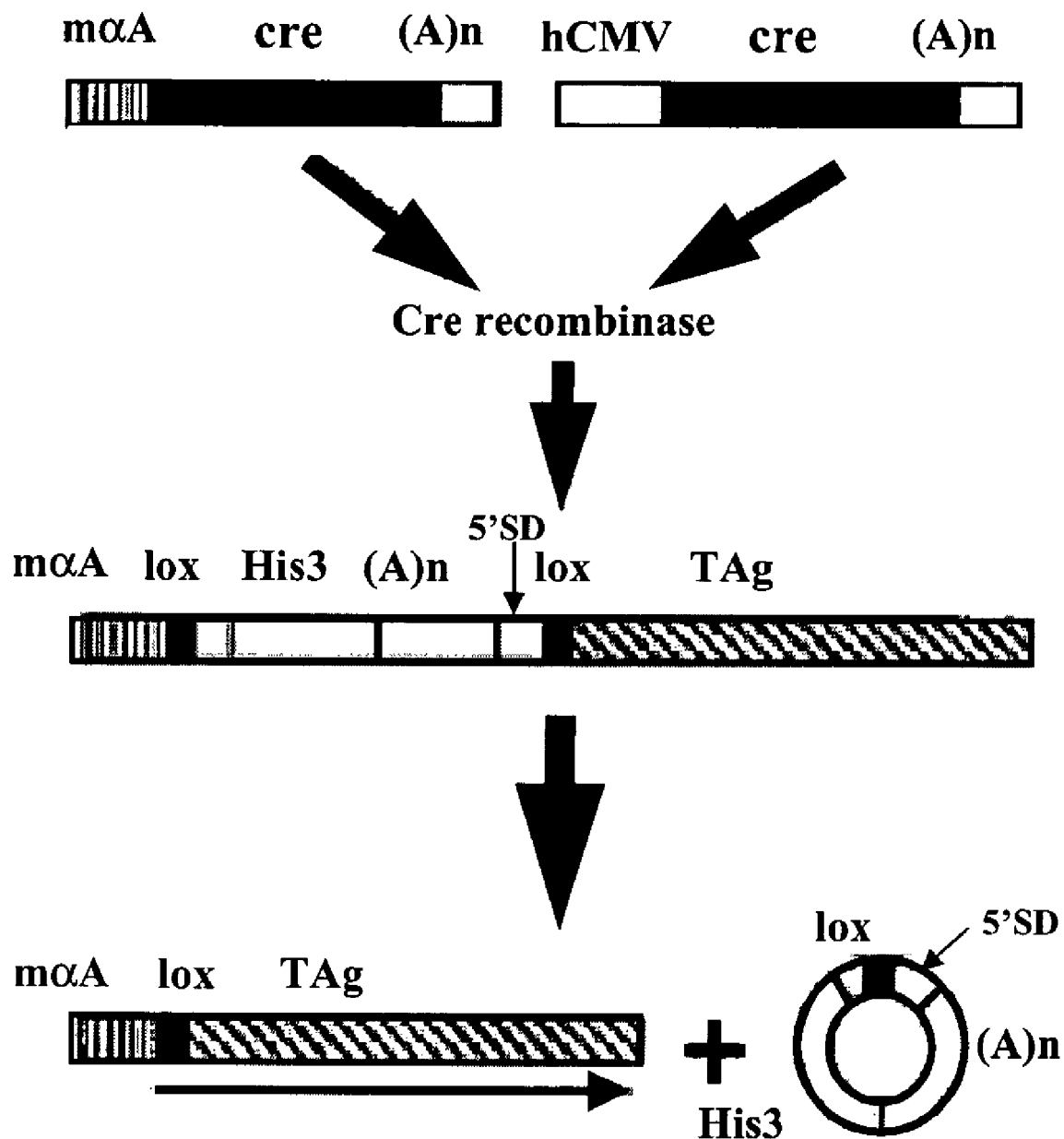
FIG. 5. Using an Enzyme System to Remove the DNA from the bead and Circularize it.

PCR or "polymerase chain reaction" is a techniques that allows the "copying" or "amplification" of a segment of DNA. PCR is routinely used in forensic, medical, and research laboratories. DNA fragments from a few hundred bp to 30,000 bp can be made, and amplifications of fragments less than 5 kb are relatively routine.

The most efficient way to obtain larger fragments (>30 kb) is by PCR amplification using specific primers to precisely define the ends and ligating the component fragments in a defined order. A way to specify the orientation in joining of PCR fragments would allow large defined arrays to be constructed without regard to the source of each PCR fragment. However, the full duplex nature of the PCR fragment does not allow the specificity of joining that can be achieved through annealing of complementary single strand ends.

A number of methods have been used for orientating PCR fragments. These generally involve the use of the extra A present at the 3' end of some PCR fragments, or inclusion of specialized sequences that can be manipulated by restriction enzymes, exonucleases or polymerases to generate a sticky end. Other methods of altering the primer so sticky ends can be formed include placement of an apurinic residue, or spacer not recognized by the PCR polymerase as a 3' blocking agent (1) (e.g., hyperthermophilic polymerases cease extension before a dU residue) (2).

The method that we have developed (3) is based on removal of part of the primer, so that a 3' overhang is produced that conveys specificity in joining to other PCR or vector fragments. The primer is made with a modified nucleotide at a specific position. It is subsequently removed by an excision repair enzyme and the chain cleaved by the action of a AP endonuclease (or lyase).

In our initial work we used deoxyuridine as the modified nucleotide and the commercially available enzyme uracil-DNA-glycosylase (4-6) and $T_4$ endonuclease V to remove the base and cleave the primer to generate a ligatable 5' phosphorylated end.

After cleavage, the 5' end of the primer is dissociated by heat to produce a protruding 3' end on the PCR fragment. The location of the modified nucleotide within the primer and the specific primer sequence allow a variety of lengths and sequences in the 3' overhang to be produced by this treatment. We have shown several such fragments can be assembled to give an in-phase, functional gene (3).

We have extended the method to allow directed sequential ligation by using a reversible attachment to a solid substrate as a scaffold on which to build the growing DNA fragment. One embodiment uses modified streptavidin-coated magnetic beads, which have been used with single stranded DNA (7). The first PCR fragment is coupled to the beads by conjugating a biotin to the first primer or first PCR fragment. Sequential PCR fragments are added to this growing chain using the excision repair generated overhang system described above.

In order to remove the growing PCR chain from the solid scaffold, we employed the cre-lox system to remove the large assembled fragment and circularize it. Cre has been shown to act on linear DNA in solution (8). The released fragment is in a circular form which allows it to be efficient for transformation as it is removed from the scaffold. In this system, the first PCR fragment contains a lox site, as does the last PCR fragment. The lox sites may be included in the primer, or be located inside (3') of the primer sites. Using the Cre enzyme allows removal and recircularization of the assembled DNA chain from the scaffold.

Additional signals can be incorporated into the assembled DNA fragments, such as an origin of replication, and a selective marker. This allows the circularized fragment to be directly transformed into a cell and selected for. In most embodiments, these signals will be contained in the first or last PCR fragment to avoid interrupting the coding sequences. However, the sites may also be placed between genes or in introns.

Example 1

All PCRs were performed using Gene Amp® reagents (PERKIN-ELMER™, Norwalk, Conn., USA) in 50 μL reaction mixtures with 2.5 U Taq DNA polymerase and 2.5 mM $MgCl_2$ in a RoboCycler Temperature Cycler (STRATAGENE™, La Jolla, Calif., U.S.A.). PCR primer sequences are shown in Table 1. Amplifications from pACYC184 (NEW ENGLAND BIOLABS™, Beverly, Mass., U.S.A.) contained 50 ng of plasmid and 40 pmol of each PCR primer CAT3 and CAT5 or SacCAT3 and SacCAT5. Cycling was at 95° C. for 1 min. 55° C. for 1 min. 72° for 1 min for 30 cycles followed by 1 cycle at 72° C. for 3 min. Genomic amplifications from *E. coli* strain W3110 contained 100 ng genomic DNA, 40 pmol of LacST#1 and #2, LacMD#1 and #2, LacEN#1 and #2 (See Table 1.) and were carried out at 95° C. for 45 s, 55° C. for 45 s, 72° C. for 45 s for 30 cycles, then a final extension at 72° C. for 3 min.

TABLE 1

PCR Primer Sequences

CAT3     (5' AGCUCGGCAC GTAAGAGGTT CCAACTTTCA CC 3' [32 nucleotide])

CAT5     (5' AGCUCCAGGC GTTTAAGGGC ACCAATAACT GC 3' [32 nt])

SacCAT3  (5' AGAATGAGCT CCAGGCGTTT AAGGGCACCA ATAACTGC 3' [38 nt])

SacCAT5  (5' TCAATGAGCT CGGCACGTAA GAGGTTCCAA CTTTCACC 3' [38 nt])

LacST#1  (5' AGCUCGCACG ACAGGTTTCC CGACTGGAAA GCGGGC 3' [36 nt])

LacST#2  (5' ACCACCACGC UCATCGATAA TTTCACCGCC G 3' [31 nt])

TABLE 1-continued

PCR Primer Sequences

```
LacMD#1  (5' AGCGTGGTGG UTATGCCGAT CGCGTCACAC 3' [30 nt])

LacMD#2  (5' AGCGCTGGAU GCGGCGTGCG GTCGGCAAAG 3' [30 nt])

LacEN#1  (5' ATCCAGCGCU GACGGAAGCA AAACACCAGC 3' [30 nt])

LacEN#2  (5' AGCUCAATAC GGGCAGACAT GGCCTGCCCG G 3' [31 nt])
```

PCR products were generated and purified from pACYC184 using primers CAT3 and CAT5 encoding the entire chloramphenicol acetyltransferase (cat) gene. Following PCR, 1 μL (1 u) of UDG (LIFE TECHNOLOGIES™, Gaithersburg, Md., USA) and 8 μL of HAPI (13 mg/mL) were added, and the PCR products incubated for 30 min at 37° C. and 15 min at 65° C., followed by the addition of spermine (0.2 mM final) with 15-min incubations at 37° C. and 15 min at 65° C. and 70° C. The enzymatically treated PCR samples were purified with QIAquick® PCR Purification Kit (QIAGEN™, Chatsworth, Calif., USA). Ligations were performed with 200 ng of the treated PCR product and 100 ng of SacI-cleaved dephosphorylated pUC19 (STRATAGENE™) overnight at 16° C. Library-efficiency competent E. coli DH5α cells (LITE TECHNOLOGIES™) were transformed according to the manufacturer's protocol and plated on LB plates containing ampicillin (Ap) and 5-bromo-4-chloro-3-indolyl-β-D-galactopyranoside (X-gal) or ampicillin and chloramphenicol (Cm) and incubated overnight at 37° C. Plasmid DNAs from at least 50 individual colonies from each type of plate were isolated using alkaline lysis, digested with SacI and characterized by electrophoresis using 0.7% agarose gels. In addition, colonies from the Ap/X-gal plates were transferred to Ap/Cm plates.

Alternatively, following UDG treatment, the PCR samples were purified with the QIAquick and then treated with HAPI in HAPI buffer (20 mM Tris-HCl, pH 8.0, 10 mM NaCl, 1 mM EDTA, 5 mM $MgCl_2$ and 10 μg heat-inactivated bovine serum albumin [BSA]) and incubated overnight at room temperature to allow for the spontaneous β elimination of the 5' dRp group.

Immediately following amplification, the CAT PCR product was treated with 1 μL of UDG, 0.5 μL (10 U) of T4 endonuclease V (EPICENTRE TECHNOLOGIES™, Madison, Wis., USA) and incubated at 37° C. for 30 min, then at 70° C. for 15 min. The PCR mixture was cleaned with QIAquick. In 20 μL, ligations using 1:1, 1:5 and 1:10 molar ratios of SacI-cleaved, dephosphorylated pUC19 (100 ng) to treated PCR product were incubated overnight at 16° C. Library-efficiency competent E. coli DH5α cells were transformed following the manufacturer's protocol and plated on Ap/X-gal or with Ap/Cm plates and incubated overnight at 37° C. Plasmid products from at least 50 individual colonies were isolated and checked as described earlier.

Primers SacCAT3 and SacCAT5 were designed, adding 5 nucleotides to the end from the SacI recognition sequence. The cat gene PCR products were purified as before and digested with SacI for 16 h at 37° C. Following digestion and enzyme inactivation, the digested PCR fragments were ligated using 1:1, 1:5 and 1:10 molar ratios with the same preparation of pUC19 used above. Library-efficiency competent E. coli DH5α cells were transformed and plated on Ap/X-gal or Ap/Cm plates. Plasmid DNAs from at least 50 colonies were isolated and checked as described.

Using genomic DNA from E Coli W3110 as template, three PCR products were generated using primers LacST#1 and #2, LacMD#1 and #2 and LacEN#1 and #2. Each PCR product was incubated with UDG and T4 endonuclease V as described. The treated PCR samples were ligated into dephosphorylated SacI-cleaved pSP72 (100 ng) (PROMEGA™, Madison, Wis., USA) at a 1:1 and 1:5 vector/insert molar ratio and transformed into library-efficiency competent E. coli DH5α cells, and the cells were plated on LB plates containing ampicillin and X-gal to test for the presence of functional β-galactosidase. Plasmid DNAs from 50 white and blue colonies were isolated and digested with either SacI, HindIII, or ClaI and separated by electrophoresis on 0.7% agarose gels. The HindIII digest shows total plasmid size, and the ClaI digest determines insert orientation and integrity of the lac operon.

Results are shown in Table 2 and the reader is referred to (3) for additional details.

TABLE 2

| Product Treatment | CAT PCR Product* Transformants per μg of Vector | LacZ PCR Product* Transformants per μg of Vector |
| --- | --- | --- |
| pUC19 transformation control | $3 \times 10^7$ | |
| pSP72 control | | $3 \times 10^7$ |
| No treatment | 0 | 0 |
| UDG only, no HAP1 | 0 | 0 |
| UDG + HAP1 with no Overnight β elimination | 0 | 0 |
| UDG + HAP1 with no Overnight β elimination | $4 \times 10^3$ | |
| UDG + HAP1 + spermine | $4.5 \times 10^3$ | |
| UDG + T4 endoV, 1:5 ratio | $8 \times 10^5$ | |
| Sac digestion, 1:5 ratio Primers with SacI site | $1 \times 10^4$ | |
| UDG + T4 endoV, 1:1 ratio 3 LacZ fragments | | $2 \times 10^5$ |
| UDG + T4 endoV, 1:1 ratio Entire lac operon | | $2 \times 10^5$ |

*Data are compiled from at least 3 ligations and transformations.

Example 2

Our first example demonstrated the viability of the method as used in solution. However, the method was cumbersome, tedious, and not applicable for large scale up. Thus, we now demonstrate a solid phase procedure that is suitable for scale-up and commercial use.

This example was based on the use of a plasmid which, intact, confers resistance to the antibiotic ampicillin and has the lacZ gene which allows for metabolism of the substrate Xgal; an E. coli host with a lacZ-containing plasmid grows as a blue colony on Xgal plates instead of a white colony which the E. coli host produces.

The first step is to design oligonucleotides so that the PCR product A will have an overhang on the 3 end opposite of the biotin and will leave a sticky 3' end after enzymatic treatment with UDG and T4 endonuclease V AND so that there is a biotin attached to the 5 end AND so that the PCR amplified product includes a loxP site near the end where biotin is attached. In our example, this product A also includes the gene which confers resistance to ampicillin.

A second set of primers are designed so that the PCR amplification product B will have a overhang after enzymatic treatment with UNG and T4 endonuclease V which is complementary to the overhang formed on PCR product A, AND so that the PCR product includes a loxP site in an appropriate arrangement near the 3 end.

PCR amplifications were performed to get products A and B and both were treated with T4 DNA polymerase in the presence of ultrapure dNTPs to be certain that the PCR products have been completed and have flush ends. A Wizard cleanup kit is used to remove extra nucleotides and enzyme. Both products are then treated with UNG and T4 endonuclease V to create overhangs. The treated products are now designated as A/U/T for the treated PCR A product and B/U/T for the treated PCR product B.

The treated fragment bearing an attached biotin, A/U/T is bound to DYNALs magnetic dynabeads with attached streptavidin; the biotin on A/U/T will bind strongly to the streptavidin. As the experiment progresses, the beads magnetic properties are used to quickly wash away reagents and enzymes, change buffer conditions, and add in new reaction components. This presents a significant commercial advantage over performing the reactions in solution and having to centrifuge the products after every washing step.

After binding a wash is used to remove unbound A/U/T. Then B/U/T is added to the beads which have bound A/U/T. A joining reaction is done to ligate A/U/T and B/U/T so that product, C, is created, and it is bound to the beads. The ligase enzyme is heat inactivated and unreacted B/U/T and ligase reaction components are washed to remove them from the bead mixture. Cre recombinase is added to the beads which have C bound, in order to circularize C using the loxP sites; circularizing detaches C from the beads and forms a product that can be used directly in transformations. Cre recombinase can then be heat inactivated and at this point the DNA can be transformed.

In this example, a restriction enzyme(s) was added which will cut any template DNA (remaining from the PCR reactions) which is contaminating the product C; this step can be used to reduce the number of blue colonies in the transformation step, making identification of white colonies (containing product C) easier. The restriction enzyme(s) are then heat inactivated.

The supernatant from the bead mixture, which contains circularized C, is used to transform E. coli cells. Selection of transformed cells is accomplished by plating the transformed cells on Xgal/Amp plates. White colonies contain the desired fragment C. Blue colonies contain the plasmid used as template for the PCR reactions.

In an experiment performed in 2000, the efficiency of the entire experiment was approximately 100,000 white colonies/ug of A/U/T on the beads. The background level of blue colonies was <1%. The optimal transformation efficiency for this host cell is 1 billion colonies/ug for simply transforming the cells with a small characterized plasmid.

The reagents used in the bead assembly method:

| Reagent | Source |
| --- | --- |
| Failsafe Polymerase for PCR | EPICENTRE ™ |
| T4 DNA polymerase | EPICENTRE ™ |
| Ultrapure dNTPs | USB ™ |
| PCR preps cleanup kit | WIZARD FROM PROMEGA ™ |
| UNG = Uracil N glycosylase | EPICENTRE ™ |
| T4 endonuclease V | EPICENTRE ™ |
| Beads with kilobase binder kit | DYNAL ™ |
| Ligase - Fast Link kit | EPICENTRE ™ |
| Cre recombinase | INVITROGEN ™ |

All citations are listed here for convenience and each is expressly incorporated by reference in its entirety for any purpose:

1. Gal J, Schnell R, Kalman M. Polymerase dependence of autosticky polymerase chain reaction. Anal Biochem. 2000 Jun. 15; 282(1):156-8. Gal J, Schnell R, Szekeres S, Kalman M. Directional cloning of native PCR products with preformed sticky ends (autosticky PCR). Mol Gen Genet. 1999 January; 260(6):569-73.5.
2. Greagg M A, Fogg M J, Panayotou G, Evans S J, Connolly B A, Pearl L H. A read-ahead function in archaeal DNA polymerases detects promutagenic template-strand uracil. Proc Natl Acad Sci USA. 1999 Aug. 3; 96(16):9045-50.
3. Watson D E, Bennett G N. Cloning and assembly of PCR products using modified primers and DNA repair enzymes. Biotechniques. 1997 November; 23(5):858-62, 864 (attached as Example 1).
4. Booth P M, Buchman G W, Rashtchian A. Assembly and cloning of coding sequences for neurotrophic factors directly from genomic DNA using polymerase chain reaction and uracil DNA glycosylase. Gene. 1994 Sep. 2; 146 (2):303-8.
5. Rashtchian A, Buchman G W, Schuster D M, Berninger M S. Uracil DNA glycosylase-mediated cloning of polymerase chain reaction-amplified DNA: application to genomic and cDNA cloning. Anal Biochem. 1992 October; 206(1):91-7.
6. Nisson P E, Rashtchian A, Watkins P C. Rapid and efficient cloning of Alu-PCR products using uracil DNA glycosylase. PCR Methods Appl. 1991 November; 1(2):120-3.
7. Stahl S, Hansson M, Ahlborg N, Nguyen T N, Liljeqvist S, Lundeberg J, Uhlen M. Solid-phase gene assembly of constructs derived from the *Plasmodium falciparum* malaria blood-stage antigen Ag332. Biotechniques 1993 March; 14(3):424-34.
8. Abremski K, Hoess R, Stemberg N. Studies on the properties of P1 site-specific recombination: evidence for topologically unlinked products following recombination. Cell. 1983 April; 32(4):1301-11

What is claimed is:

1. A method of assembling PCR fragments, comprising
a) making a first PCR fragment with first and second primers, wherein the second primer comprises a modified nucleotide that can be removed by a DNA repair enzyme, resulting in a 3' overhang, and wherein the first PCR fragment comprises a first site specific recombinase site;
b) treating the first PCR fragment with a DNA repair enzyme to generate a 3' overhang and immobilizing the first PCR fragment on a solid support or vice versa;
c) making a second PCR fragment with third and fourth primers, wherein the third and fourth primers each comprises a modified nucleotide that can be removed by a DNA repair enzyme resulting in a 3' overhang;
d) treating the second PCR fragment with a DNA repair enzyme to generate a 3' overhang;
e) annealing and ligating the first and second PCR fragments;
f) optionally repeating steps c, d and e until a last PCR fragment is added to the growing chain to produce an assembled fragment, wherein the last PCR fragment comprises a second site specific recombinase site; and
g) simultaneously removing and circularizing the assembled fragment from the solid support with a site specific recombinase in a single step.

2. The method of claim 1, where one of the PCR fragments comprises an origin of replication and a selectable marker.

3. The method of claim 1, wherein the first PCR fragment or the last PCR fragment comprises an origin of replication and a selectable marker.

4. The method of claim 1, wherein the site specific recombinase is CRE and the site specific recombinase site is lox.

5. The method of claim 1, wherein the nucleotide is deoxyuridine and the DNA repair enzyme is uracil-DNA-glycosylase followed by $T_4$ endonuclease V.

6. The method of claim 5, wherein the assembled DNA is greater than 30 kb.

7. The method of claim 5, wherein the assembled DNA is greater than 30, 40, 50, 75, 100, 125, 150, 200, 250, 300, 350, 400, 450, 500, 750, 1000 or 1500 kb.

* * * * *

SEQUENCE LISTING

<160> NUMBER OF SEQ ID NOS: 10

<210> SEQ ID NO 1
<211> LENGTH: 32

```
<212> TYPE: DNA
<213> ORGANISM: Artificial
<220> FEATURE:
<223> OTHER INFORMATION: Primer Sequence
<220> FEATURE:
<221> NAME/KEY: misc_feature
<222> LOCATION: (4)..(4)
<223> OTHER INFORMATION: wherein n is deoxyuridine

<400> SEQUENCE: 1
agcncggcac gtaagaggtt ccaactttca cc                                32

<210> SEQ ID NO 2
<211> LENGTH: 32
<212> TYPE: DNA
<213> ORGANISM: Artificial
<220> FEATURE:
<223> OTHER INFORMATION: Primer Sequence
<220> FEATURE:
<221> NAME/KEY: misc_feature
<222> LOCATION: (4)..(4)
<223> OTHER INFORMATION: wherein n is deoxyuridine

<400> SEQUENCE: 2
agcnccaggc gtttaagggc accaataact gc                                32

<210> SEQ ID NO 3
<211> LENGTH: 38
<212> TYPE: DNA
<213> ORGANISM: Artificial
<220> FEATURE:
<223> OTHER INFORMATION: Primer Sequence

<400> SEQUENCE: 3
agaatgagct ccaggcgttt aagggcacca ataactgc                          38

<210> SEQ ID NO 4
<211> LENGTH: 38
<212> TYPE: DNA
<213> ORGANISM: Artificial
<220> FEATURE:
<223> OTHER INFORMATION: Primer Sequence

<400> SEQUENCE: 4
tcaatgagct cggcacgtaa gaggttccaa ctttcacc                          38

<210> SEQ ID NO 5
<211> LENGTH: 36
<212> TYPE: DNA
<213> ORGANISM: Artificial
<220> FEATURE:
<223> OTHER INFORMATION: Primer Sequence
<220> FEATURE:
<221> NAME/KEY: misc_feature
<222> LOCATION: (4)..(4)
<223> OTHER INFORMATION: wherein n is deoxyuridine

<400> SEQUENCE: 5
agcncgcacg acaggtttcc cgactggaaa gcgggc                            36

<210> SEQ ID NO 6
<211> LENGTH: 31
<212> TYPE: DNA
<213> ORGANISM: Artificial
<220> FEATURE:
<223> OTHER INFORMATION: Primer Sequence
<220> FEATURE:
```

<221> NAME/KEY: misc_feature
<222> LOCATION: (11)..(11)
<223> OTHER INFORMATION: wherein n is deoxyuridine

<400> SEQUENCE: 6
accaccacgc ncatcgataa tttcaccgcc g                          31

<210> SEQ ID NO 7
<211> LENGTH: 30
<212> TYPE: DNA
<213> ORGANISM: Artificial
<220> FEATURE:
<223> OTHER INFORMATION: Primer Sequence
<220> FEATURE:
<221> NAME/KEY: misc_feature
<222> LOCATION: (11)..(11)
<223> OTHER INFORMATION: wherein n is deoxyuridine

<400> SEQUENCE: 7
agcgtggtgg ntatgccgat cgcgtcacac                            30

<210> SEQ ID NO 8
<211> LENGTH: 30
<212> TYPE: DNA
<213> ORGANISM: Artificial
<220> FEATURE:
<223> OTHER INFORMATION: Primer Sequence
<220> FEATURE:
<221> NAME/KEY: misc_feature
<222> LOCATION: (10)..(10)
<223> OTHER INFORMATION: wherein n is deoxyuridine

<400> SEQUENCE: 8
agcgctggan gcggcgtgcg gtcggcaaag                            30

<210> SEQ ID NO 9
<211> LENGTH: 30
<212> TYPE: DNA
<213> ORGANISM: Artificial
<220> FEATURE:
<223> OTHER INFORMATION: Primer Sequence
<220> FEATURE:
<221> NAME/KEY: misc_feature
<222> LOCATION: (10)..(10)
<223> OTHER INFORMATION: wherein n is deoxyuridine

<400> SEQUENCE: 9
atccagcgcn gacggaagca aaacaccagc                            30

<210> SEQ ID NO 10
<211> LENGTH: 31
<212> TYPE: DNA
<213> ORGANISM: Artificial
<220> FEATURE:
<223> OTHER INFORMATION: Primer Sequence
<220> FEATURE:
<221> NAME/KEY: misc_feature
<222> LOCATION: (4)..(4)
<223> OTHER INFORMATION: wherein n is deoxyuridine

<400> SEQUENCE: 10
agcncaatac gggcagacat ggcctgcccg g                          31